(12) United States Patent
Yamada et al.

(10) Patent No.: US 6,921,745 B2
(45) Date of Patent: Jul. 26, 2005

(54) BACTERICIDAL COMPOSITION COMPRISING POLYLYSINE AND A PLANT ESSENTIAL OIL

(75) Inventors: Hiroyuki Yamada, Tokyo (JP); Hirohiko Ishida, Tokyo (JP); Kazunori Tsukuda, Wakayama (JP)

(73) Assignee: Kao Corporation, Tokyo (JP)

(*) Notice: Subject to any disclaimer, the term of this patent is extended or adjusted under 35 U.S.C. 154(b) by 18 days.

(21) Appl. No.: 10/473,447

(22) PCT Filed: Apr. 15, 2002

(86) PCT No.: PCT/JP02/03734

§ 371 (c)(1),
(2), (4) Date: Sep. 30, 2003

(87) PCT Pub. No.: WO02/085109

PCT Pub. Date: Oct. 31, 2002

(65) Prior Publication Data

US 2004/0132630 A1 Jul. 8, 2004

(30) Foreign Application Priority Data

Apr. 17, 2001 (JP) ........................................ 2001-117961
Feb. 26, 2002 (JP) ........................................ 2002-049079

(51) Int. Cl.⁷ ............................. C11D 3/382; C11D 3/33
(52) U.S. Cl. ........................ 510/463; 510/251; 510/344; 510/382; 510/398; 510/420; 510/434; 510/462; 510/463; 510/477; 510/480
(58) Field of Search .................................. 510/251, 344, 510/382, 398, 420, 434, 462, 477, 480

(56) References Cited

FOREIGN PATENT DOCUMENTS

| JP | 2-107174 | | 4/1990 |
|----|----------|---|--------|
| JP | 7-166200 | | 6/1995 |
| JP | 7-188696 | | 7/1995 |
| JP | 8-319208 | | 12/1996 |
| JP | 09 040516 | | 2/1997 |
| JP | 09 176689 | | 7/1997 |
| JP | 11 061639 | | 3/1999 |
| JP | 11-061639 | * | 5/1999 |
| JP | 2000-26885 | | 1/2000 |
| JP | 2000-26889 | | 1/2000 |
| JP | 2000 026886 | | 1/2000 |
| JP | 2000 026887 | | 1/2000 |
| WO | 00/11956 | * | 3/2000 |
| WO | 00 11956 | | 3/2000 |

* cited by examiner

*Primary Examiner*—Charles Boyer
(74) *Attorney, Agent, or Firm*—Oblon, Spivak, McClelland, Maier & Neustadt, P.C.

(57) ABSTRACT

This invention provides an easily handled bactericide composition necessitating no rinsing step after treatment and exhibiting a safe and excellent bactericidal effect on surfaces which may be brought into direct contact with foods, such as hard surfaces in a house other than dishes and cooking devices. The bactericide composition of this invention comprises (a) polylysine, (b) plant essential oil, (c) organic solvent and (d) water in a specified ratio.

10 Claims, No Drawings

BACTERICIDAL COMPOSITION COMPRISING POLYLYSINE AND A PLANT ESSENTIAL OIL

TECHNICAL FIELD OF THE INVENTION

This invention relates to a bactericide composition suitable as a bactericide for hard surfaces in a house, such as the surfaces of a kitchen table, a sink, a wall, a floor such as flooring, and furniture.

PRIOR ARTS

As the living environment is changed in recent years, the way of thinking on cleanliness is changing. In particular, there is an increasing interest in disinfection, and those who worrying about the influence of a large number of microorganisms present on the surfaces of a kitchen table, a sink, a wall, a floor and furniture in a room are increasing in number. Wiping is an effective method of inhibiting the occurrence of these microorganisms, but for sufficiently inhibiting the increase of microorganisms, methods of inhibiting the occurrence of microorganisms or inhibiting the growth of microorganisms by sterilization, disinfection etc. are preferably used in combination.

A wide variety of substances, whether organic or inorganic, have been found as bactericides, and a large number of bactericides occur in the nature. Among these, a natural bactericide polylysine can be used as a preservative for foods, and further use thereof as a bactericidal detergent for foods and dishes has been proposed.

JP-A No. 9-176689 describes a bactericidal detergent for dishes or foods such as vegetables and fruits, which comprises polylysine/chelating agent/surfactant/solubilizing agent. Besides, bactericidal detergents for foods are known according to JP-A Nos. 2000-26885, 2000-26886, 2000-26887, 2000-26889 and 7-188696. JP-A Nos. 2-107174 and 8-319208 disclose a food bactericide of aerosol type comprising polylysine incorporated into ethanol as the base. For use not directed to foods, JP-A No. 7-166200 describes a toilet detergent comprising polylysine. However, incorporation of ethanol as a bactericide in a large amount is not preferable for fire prevention, and there is demand for an easily handled bactericide having a safe and excellent bactericidal effect.

DISCLOSURE OF INVENTION

The object of this invention is to provide an easily handled bactericide composition exhibiting a safe and excellent bactericidal effect on hard surfaces which may be brought into contact with foods, for example on the hard surfaces of a kitchen table, a sink, a wall, a floor, furniture and electric appliances other than dishes and cooking devices in a house, particularly on the surfaces of a kitchen table and a refrigerator or therearound.

This invention provides a bactericide composition comprising (a) 0.0001 to 1% by mass of polylysine [referred to hereinafter as component (a)], (b) 0.0001 to 1% by mass of a plant essential oil [referred to hereinafter as component (b)], (c) 0.1 to 18% by mass of an organic solvent [referred to hereinafter as component (c)] and (d) 80 to 99% by mass of water [referred to hereinafter as component (d)].

Further, this invention provides a bactericide composition comprising (a) 0.0001 to 1% by mass of polylysine, (b1) 0.0001 to 1% by mass of at least one compound selected from the group consisting of thymol, geraniol, hinokithiol, carvacrol, citral, eugenol, terpinene (terpinene)-4-ol, 1,8-cineol, citronellal, citronellol, linalool, anethole, menthol, menthone, carvone, camphor and limonene [referred to hereinafter as component (b1)], (c) 0.1 to 18% by mass of an organic solvent and (d) 80 to 99% by weigh of water.

Furthermore, this invention provides a packaged bactericide comprising a bactericide composition comprising the above components (a) to (d), with a surfactant content of not higher than 0.1% by mass, charged into a container equipped with a non-aerosol sprayer such as manually operated sprayer.

Moreover, this invention provides a method of sterilizing a hard surface by using a composition comprising the above components (a) to (d).

In the invention, the content of a surfactant may be not higher than 0.1% by mass.

In this invention, sterilization has a broad meaning including not only microbial sterilization but also inhibition of microbial growth.

The invention further provides use of the composition as defined above as sterilizer and then a method of sterilizing a hard surface, comprising applying the composition as above defined to the hard surface and wiping the composition out of the hard surface.

DETAILED EXPLANATION OF INVENTION

<Component (a)>

Polylysine as component (a) used in this invention is a bactericidal component and may be either α-polylysine or ε-polylysine, but in this invention, ε-polylysine is used preferably for safety. The polylysine, which is obtained by culturing a microorganism of the genus Streptomyces, is a polypeptide produced through condensation of lysine as an essential amino acid for the human body. The polylysine may be used in a free form or as an organic or inorganic salt thereof. Polylysine blended with excipients or fillers for easy handling can also be used.

The present inventors found that for effectively disinfecting a polluted hard surface by wiping, it is important that:
1) a compounded solution can suitably spread on a surface to be cleaned while moistening the surface,
2) the amount of the remaining compounded solution containing contaminants is minimized at the time of wiping, whereby the residual contaminants serving as nutrients for bacteria are reduced to inhibit bacterial growth, and
3) after wiping, its antimicrobial agent remains in an amount enough to disinfect the surface.

The inventors further found that these requirements can be satisfied effectively when the compounded solution can be adsorbed onto the hard surface and render the hard surface suitably hydrophobic upon adsorption. From this point of view, the inventors found that the bactericide composition of this invention blended with polylysine is effective.

By incorporation of polylysine, the composition of this invention upon spraying onto a surface to be treated can confer suitable wetting properties on the surface thereby uniformly sterilizing the surface sprayed with the composition. After the composition is sprayed, polylysine is absorbed onto the treated surface thereby endowing the surface with such suitable repellency as to repel water in the composition, whereby pollutant-containing water is easily transferred upon wiping into a wiper so that after wiping, the amount of the pollutant-containing water remaining on the surface is reduced. Further, because the hydrophobicity conferred on the surface by the composition of this invention is not high, the composition remains in a small but sufficient amount to sterilize the surface. As described above, the inventors found that the composition of this invention comprising polylysine satisfies the contradicting prescribed properties necessary for disinfecting the surface by wiping thereby bringing about a particularly outstanding effect.

In the composition of this invention, an ingredient for further improving the antimicrobial performance of polylysine should have the following properties:
1) the ingredient has less influence on the ability of polylysine to confer suitable hydrophobicity on a surface to be treated, and
2) the ingredient does not influence the antimicrobial property of polylysine. The inventors found that as a base having such properties, a specific plant essential oil and its components are effective. By combining these components with polylysine, the polylysine can be endowed with a higher disinfection ability without deterioration of the above-described properties thereof.

When the composition does not contain polylysine, the composition is inferior in bactericidal action, while pollutant-containing water remains easily upon wiping, thus deteriorating the outer appearance of the treated surface and significantly reducing the action of the antimicrobial agent after treatment.

The bactericide composition of this invention comprises polylysine as component (a) in an amount of 0.0001 to 1% by mass for sterilizing properties, preferably 0.0005 to 0.05% by mass for achieving good wiping ability.

<Component (b)>

The component (b) is a plant essential oil, that is, a vegetable essential oil, such as tree essential, herb essential and fruit essential.

Many plant essential oils used as component (b) exhibit a bactericidal action, but those preferably used in this invention are anise oil, origanum (oregano) oil, orange oil, lemon oil, lime oil, grapefruit oil, mandarin oil, citronella oil, cassia oil, camomile oil, mustard oil, garlic oil, caraway oil, cumin, clove, coriander, cinnamon oil, spearmint oil, sage oil, sage clary oil, geranium oil, thyme oil, basil oil, peppermint oil, birch (white birch) oil, Palma Rosa oil, hiba or hinoki (white-cedar) oil, pimento (allspice), bay oil, petigrain oil, peppermint oil, bergamot oil, neroli oil, eucalyptus oil, lavandine oil, lavender oil, lemon oil, lemongrass oil, rosemary oil, laurel, and Japanese horseradish oil, and these are used singly or as a mixture. It is preferable to employ plant essential oils containing thymol, geraniol, hinokithiol, carvacrol, citral, eugenol, terpinene (terpinene)-4-ol, 1,8-cineol, linalool, anethole, menthol, menthone, carvone, camphor, limonene, α-pinene, β-pinene, citronellal, citronellol, phenyl ethyl alcohol and benzyl alcohol as components in the plant essential oil used in this invention, and these are used singly or as a mixture.

As the component (b1) contained in the plant essential oil in this invention, use can be made of at least one compound selected from the group consisting of thymol, geraniol, hinokithiol, carvacrol, citral, eugenol, terpinene (terpinene)-4-ol, 1,8-cineol, citronellal, citronellol, linalool, anethole, menthol, menthone, carvone, camphor and limonene, more preferably thymol, geraniol, hinokithiol, carvacrol, citral, eugenol, terpinene (terpinene)-4-ol and 1,8-cineol, further preferably thymol, geraniol, citral and 1,8-cineol.

In this invention, the plant essential oil as the component (b); and the component (b1), can also be used in combination.

The bactericide composition of this invention comprises (b) and/or (b1) in an amount of 0.001 to 1% by mass, preferably 0.0001 to 0.5% by mass for sterilizing properties, or preferably 0.0001 to 0.1% by mass for wiping ability.

<Component (c)>

The composition of this invention further comprises an organic solvent as the component (c) for the purpose of solubilizing the plant essential oil and promoting drying of an intended hard surface. The organic solvent is preferably the one having a boiling point of 100° C. or less at which it can form an azeotropic mixture with water, and for example, ethanol, propanol, isopropanol etc. can be mentioned, and in particular ethanol is preferable. In consideration of drying rate, wiping ability and safety, the amount of the organic solvent as the component (c) in the bactericide composition is 0.1 to 18% by mass, preferably 1 to 10% by mass, and more preferably 1 to 8% by mass. When ethanol is used, modified ethanol can be used, and the modified ethanol includes 8-acetylated sucrose-modified ethanol, polyoxyethylene alkyl ether-modified ethanol, and flavor-modified ethanol.

To achieve good stability of the solution in this invention, the ratio (ratio by mass) of the component (b) and/or the component (b1) to the component (c) in the composition, that is, [component (b) and/or component (b1)]/component (c), is not higher than 1/50, preferably not higher than 1/100.

<Other Component>

The bactericide composition of this invention may further comprise a small amount of a surfactant in order to improve sterilizing properties or to disperse the component (b) stably in the composition.

Examples of the surfactant include anionic surfactants, nonionic surfactants, amphoteric surfactants or cationic surfactants.

As the anionic surfactants, those described on page 8, paragraph 0045 to page 9, paragraph 0054 in JP-A No. 9-310091 can be used, and among them, those having an alkyl group containing 8 to 22 carbon atoms, preferably 10 to 18 carbon atoms can be mentioned, and examples thereof include a linear alkyl benzene sulfonic acid, an alkyl sulfate, a polyoxyethylene alkyl ether sulfate having about 1 to 10 moles of ethylene oxide (referred to hereinafter as EO), a polyoxyethylene alkyl ether carboxylic acid having about 1 to 10 moles of EO, and a polyoxyethylene alkyl amide ether carboxylic or fatty acid having about 1 to 10 moles of EO, as well as potassium, sodium, magnesium and alkanolamine salts thereof.

As the nonionic surfactants, those described on page 6, paragraph 0028 to page 8, paragraph 0043 in JP-A No. 9-310091 can be mentioned, and among them, the following compounds are mentioned: a polyoxyethylene alkyl ether having an alkyl chain containing 8 to 22 carbon atoms, preferably 10 to 18 carbon atoms and having about 1 to 30 moles, particularly 4 to 20 moles of EO, a polyoxyethylene oxypropylene alkyl ether having about 1 to 30 moles, preferably 1 to 20 moles of EO and about 1 to 10 moles, particularly 1 to 5 moles of propylene oxide (referred to hereinafter as PO), a fatty acid alkanol amide containing about 8 to 22 carbon atoms, particularly 10 to 18 carbon atoms to which about 1 to 3 moles of EO (or PO) may be added, and an alkyl polyglucoside having an alkyl chain containing 8 to 22 carbon atoms, particularly 10 to 18 carbon atoms and having about 1.0 to 10 sugars, particularly 1.0 to 2.0 sugars condensed therein. Further, an ester between a fatty acid containing 8 to 22 carbon atoms, particularly 10 to 18 carbon atoms and a polyvalent alcohol having a hydrocarbon group containing 2 to 10 carbon atoms and 2 to 8 hydroxy groups can also be used, and specifically, glycerin fatty acid ester, polyglycerin fatty acid ester, sorbitan fatty acid ester, sucrose fatty acid ester and propylene glycol fatty acid ester can be mentioned as preferable compounds.

The amphoteric surfactants include those described on page 6, paragraphs 0023 to 0027 in JP-A No. 9-310091, and among them, those having an alkyl group containing 8 to 22 carbon atoms can be mentioned, and examples thereof include alkyl amidopropyl-N,N-dimethyl acetate betaine (N-alkanoyl aminopropyl-N,N-dimethyl-N-carboxymethyl ammonium carbobetaine), alkyl amidopropyl-N,N-dimethyl-2-hydroxypropyl sulfobetaine (N-alkanoyl aminopropyl-N,N-dimethyl-N-(2-hydroxy-3-sulfopropyl) ammonium sulfobetaine), alkyl-N,N-dimethyl acetate betaine (N-alkyl-N,N-dimethyl-N-carboxymethyl ammonium carbobetaine), alkyl amidopropyl-N,N-dimethyl-2-propyl sulfobetaine (N-alkanoyl aminopropyl-N,N-dimethyl-N-(2-sulfopropyl) ammonium sulfobetaine), lauryl-N,N-dimethyl-hydroxypropyl sulfobetaine (N-lauryl-N,N-dimethyl-N-(2-hydroxy-3-sulfopropyl) ammonium sulfobetaine), and alkyl amine oxide. Among these, the following compounds are preferable in respect of detergency: lauric acid amidopropyl-N,N-dimethyl acetate betaine (N-lauroyl aminopropyl-N,N-dimethyl-N-carboxymethyl ammonium carbobetaine), myristic acid amidopropyl-N,N-dimethyl acetate betaine (N-myristyloyl aminopropyl-N,N-dimethyl-N-carboxymethyl ammonium carbobetaine), cocamide amide propyl-N,N-dimethyl acetate betaine (N-coconut composition alkanoyl aminopropyl-N,N-dimethyl-N-carboxymethyl ammonium carbobetaine), lauryl-N,N-dimethyl-2-hydroxypropyl sulfobetaine (N-lauryl-N,N-dimethyl-N-(2-hydroxy-3-sulfopropyl) ammonium sulfobetaine), lauric acid amide propyl-N,N-dimethyl-23-hydroxypropyl betaine (N-lauroyl aminopropyl-N,N-dimethyl-N-(2-hydroxy-3-sulfopropyl) ammonium sulfobetaine), and an alkyl amine oxide having two alkyl groups containing 2 or less carbon atoms and one long-chain alkyl group containing 8 to 22 carbon atoms which may have an amide linkage.

The cationic surfactants which can be used include those described on page 3, paragraph 0012 to page 5, paragraph 0022 in JP-A No. 9-310091, and those particularly preferably used include a long-chain dialkyl dimethyl ammonium salt, long-chain monoalkyl monobenzyl dimethyl ammonium salt and monoalkyl trimethyl ammonium salt having a long alkyl chain containing 6 to 24 carbon atoms, preferably 6 to 18 carbon atoms which may be interrupted therein with an amide or ester linkage, and the counterion thereof is preferably a halogen ion, sulfate ion, or alkyl sulfate containing 1 to 3 carbon atoms. The cationic surfactants of amine type include long-chain dialkyl monomethylamine salts having a long alkyl chain containing 8 to 24 carbon atoms which may be interrupted therein with an amide or ester linkage, and preferable examples are hydrochlorides, sulfates or phosphates.

Out of the surfactants described above, the composition of the invention may include a small amount of at least one surfactant selected from:
(1) fatty acid containing 10 to 18 carbon atoms, or salts thereof,
(2) ester between a fatty acid containing 10 to 18 carbon atoms and a polyvalent alcohol having a hydrocarbon group containing 2 to 8 carbon atoms and 2 to 6 hydroxy groups,
(3) alkyl polyglucoside having an alkyl chain containing 8 to 22 carbon atoms having about 1.0 to 2.0 sugars condensed therein,
(4) alkyl amine oxide having 2 alkyl groups containing 2 or less carbon atoms and a long-chain alkyl group containing 8 to 22 carbon atoms which may have an amide linkage, and
(5) long dialkyl dimethyl ammonium salt, long monoalkyl monobenzyl dimethyl ammonium salt or monoalkyl trimethyl ammonium salt having an alkyl chain containing 6 to 18 carbon atoms.

Particularly, the surfactants (2), (3) and (5) are preferable.

Addition of the surfactant particularly the ionic surfactant in a large amount is not preferable because of its significant inhibition of the characteristics of polylysine, and for achieving a higher effect at a lower concentration of polylysine, the content of the surfactant in the bactericide composition is preferably 1% by mass or less, more preferably 0.5% by mass or less, and most preferably 0.1% by mass or less for wiping ability. Because the anionic surfactant has an influence on the bactericidal properties, the concentration of the anionic surfactant in the composition is preferably 0.1% by mass or less, more preferably 0.01% by mass or less.

Unless the desired performance is deteriorated, the bactericide composition of this invention can be compounded with various additives such as coloring matters, inorganic salts, pH adjusting agents including polycarboxylic acids, and perfumes other than the plant essential oil, but for sterilizing surfaces contacted directly with foods, these additives are preferably those for use in foods, and the amount of such additives should be minimized. When a polycarboxylic acid (succinic acid, citric acid etc.) is used as the pH adjusting agent, the polycarboxylic acid is contained in an amount of preferably 0.9% by mass or less, more preferably 0.01 to 0.9% by mass or less and most preferably 0.01 to 0.5% by mass in the composition.

The bactericide of this invention is prepared by adding water as the component (d) to the above-described essential components and arbitrary components. Accordingly, water is the Balance of the components (a) to (c) plus arbitrary components in the composition, and water is contained specifically in an amount of 80 to 99% by mass, preferably 80 to 98% by mass and more preferably 91 to 95% by mass in the composition. To demonstrate safe and excellent bactericidal properties, the pH value of the composition at 20° C. is preferably 6.0 to 9.0, more preferably 6.0 to 8.0.

The method of using the bactericide composition of this invention is preferably (1) a method of directly spraying an intended surface with the composition by a manually operated sprayer, which may be followed by wiping it off with a towel or tissue paper, (2) a method of applying the composition from a squeezable container onto an intended surface and then wiping it off with a towel or tissue paper, or (3) a method of wiping an intended surface with a towel or tissue paper previously impregnated with the composition.

The manually operated sprayer is preferably a sprayer with a manually operated trigger or a manually operated pump, particularly preferably a sprayer with a manually operated trigger. The bactericide composition of this invention is used most preferably after charged into a container equipped with such a manually operated sprayer. The sprayer is preferably the one jetting 0.1 to 1.5 g treating agent, preferably 0.2 to 1.0 g, particularly preferably 0.25 to 0.8 g by spraying it once. As the manually operated trigger, not only generally used triggers of directly hydraulic type but also triggers of hydraulic accumulator type disclosed in JP-U No. 4-37554 and JP-A No. 9-122547 can be used.

The best mode of this invention is as follows.

A bactericide composition comprising:
component (a): 0.0001 to 0.05% by mass of ε-polylysine,
component (b): 0.0001 to 0.1% by mass of at least one compound selected from the group consisting of thymol, geraniol, hinokithiol, carvacrol, citral, eugenol, terpinene (terpinene)-4-ol, 1,8-cineol, citronellal, citronellol, linalool, anethole, menthol, menthone, carvone, camphor and limonene, or a plant essential oil containing at least one compound of the above, component (c): 1 to 8% by mass of at least one member selected from the group consisting of ethanol, propanol and isopropanol, and component (d): 91 to 98% by mass of water, wherein component (b)/component (c) is not higher than 1/50, and the concentration of a surfactant is not higher than 0.1% by mass, and the content of other components is not higher than 1% by mass, as well as a packaged bactericide comprising the bactericide composition charged into a container equipped with a manually operated sprayer.

EXAMPLE

Examples 1 to 10 and Comparative Examples 1 to 6

The bactericide compositions shown in Table 1 were prepared and evaluated in the following manner for (1) sterilizing properties, (2) smell during use and feeling in use during wiping and washing, and (3) storage stability. The results are shown in Table 1.

(1) Sterilizing Properties

The sterilizing properties were examined according to a suspension test method (quantitative examination) described in "Boukin Boubai Handbook" (Handbook of Antimicrobial Antifungal Agents) (compiled by The Society for Antibacterial and Antifungal Agents, Japan and published by Gihodo Shuppan Co., Ltd.). That is, 50 $\mu$l of $10^8$ to $10^{10}$ cfu/ml microbial suspension was added to 2 ml of each composition shown in Table 1, mixed well and left for 5 minutes. Then, 10 $\mu$L of the mixture was collected and added to and mixed sufficiently with 150 $\mu$L SCDLP liquid medium, and cultured at 30° C. for 48 hours. The medium was examined for turbidity with naked eyes and evaluated according to the following criteria. As the microorganism, two kinds of microorganisms i.e. *Escherichia coli* and yellow *Staphylococcus* were used.

○: The mediums for both of *Escherichia coli* and yellow *Staphylococcus* are not turbid.

Δ: The mediums for both of *Escherichia coli* and yellow *Staphylococcus* are slightly turbid.

X: The mediums for both of *Escherichia coli* and yellow *Staphylococcus* are apparently turbid.

(2) Smell During Use and Feeling in Use During Wiping and Washing

Using trigger-type sprayer for "Kantan My Pet, which is a all-pourpouse liquid cleaner produced by Kao Corporation, an intended surface (1 m×1 m wood piece) was sprayed 5 times with the bactericide composition and then wiped with a cotton towel of 20 cm×20 cm, during which the composition was evaluated for its moistening and spreading, its wiping ability and its remaining solution according to the following criteria:

(Smell During Use)

○: Slight smell with ethanol smell unnoticed.

X: Unpleasant with strong ethanol smell.

(Moistening and Spreading of the Compounded Solution)

○: Uniform moistening and spreading on the used surface.

X: The solution is sticky to fail to achieve sufficient moistening and spreading.

(Wiping Ability of the Compounded Solution)

○: The solution on the used surface can be sufficiently wiped off.

Δ: The solution is slightly poor in the wiping ability with slight streaks occurring upon wiping.

XA: The solution cannot be sufficiently wiped off because of rapid drying during wiping.

XB: The solution cannot be sufficiently wiped off with streaks occurring upon wiping.

(Residual Solution on the Wiped Surface)

○: A suitable amount of the solution remains uniformly and thinly, and does not feel sticky after drying.

Δ: A relatively large amount of the solution remains, and feels slightly sticky after drying.

XA: The residual solution is not uniform, and the amount thereof is too low.

XB: The solution is poor in the wiping ability, and the amount thereof is too high.

(3) Storage Stability

The bactericide composition charged into a glass bottle with a plastic cap was left at 50° C. for 20 days, then observed with naked eyes and evaluated according to the following criteria. Any bactericide compositions just after prepared were in the form of transparent solutions.

○: Transparent solution.

Δ: Slightly turbid.

X: Separated.

TABLE 1

| | Example | | | | | | | | | |
|---|---|---|---|---|---|---|---|---|---|---|
| | 1 | 2 | 3 | 4 | 5 | 6 | 7 | 8 | 9 | 10 |
| Composition (weight %) component (a) | | | | | | | | | | |
| ε-polylysine | 0.01 | 0.02 | 0.01 | 0.01 | 0.02 | 0.02 | 0.02 | 0.02 | 0.1 | 0.02 |
| component (b) | | | | | | | | | | |
| Thyme oil | 0.01 | 0.01 | | 0.01 | | | | 0.005 | 0.01 | 0.1 |
| Rosemary oil | | | 0.01 | | | 0.01 | 0.01 | 0.005 | | |
| Eucalyptus oil | | | | | 0.01 | | | | | |
| component (c) | | | | | | | | | | |
| Ethanol | 5 | 8 | 5 | 5 | 8 | 5 | 5 | 5 | 5 | 3 |
| component (d) | | | | | | | | | | |
| Water | Balance | Balance | Balance | Balance | Balance | Balance | Balance | Balance | Balance | Balance |
| Alkyl (C12) polyglucoside | | | | 0.5 | | 0.5 | 0.05 | | | |

TABLE 1-continued

| | | | | | | | | | | |
|---|---|---|---|---|---|---|---|---|---|---|
| (average sugar condensation: 1.3) | | | | | | | | | | |
| Citric acid | | | | | | | | | 0.02 | |
| Total | 100 | 100 | 100 | 100 | 100 | 100 | 100 | 100 | 100 | 100 |
| pH (20° C.) | 7.2 | 7.6 | 7.2 | 7.9 | 7.6 | 7.8 | 7.8 | 7.7 | 6.8 | 7.7 |
| Sterilizing effect | ○ | ○ | ○ | ○ | ○ | ○ | ○ | ○ | ○ | ○ |
| Smell during use | ○ | ○ | ○ | ○ | ○ | ○ | ○ | ○ | ○ | ○ |
| Moistening and spreading of the compounded solution | ○ | ○ | ○ | ○ | ○ | ○ | ○ | ○ | ○ | ○ |
| Wiping ability of the compounded solution | ○ | ○ | ○ | Δ | ○ | Δ | ○ | ○ | ○ | ○ |
| Residual solution on the wiped surface | ○ | ○ | ○ | Δ | ○ | Δ | ○ | ○ | ○ | ○ |
| Storage ability | ○ | ○ | ○ | ○ | ○ | ○ | ○ | ○ | ○ | Δ |

| | Comparative Example | | | | | |
|---|---|---|---|---|---|---|
| | 1 | 2 | 3 | 4 | 5 | 6 |
| Composition (weight %) component (a) | | | | | | |
| ε-polylysine | 0.01 | | 0.01 | | | 0.02 |
| component (b) | | | | | | |
| Thyme oil | 0.01 | 0.01 | | 0.01 | 0.005 | |
| Rosemary oil | | | | | 0.005 | |
| Eucalyptus oil | | | | | | |
| component (c) | | | | | | |
| Ethanol | 30 | 5 | 5 | 5 | 5 | 8 |
| component (d) | | | | | | |
| Water | Balance | Balance | Balance | Balance | Balance | Balance |
| Alkyl (C12) polyglucoside (average sugar condensation: 1.3) | | | | 1.5 | | |
| Citric acid | | | | | | |
| Total | 100 | 100 | 100 | 100 | 100 | 100 |
| pH (20° C.) | 7.2 | 6.8 | 7.2 | 6.8 | 6.8 | 7.6 |
| Sterilizing effect | ○ | X | Δ | X | X | Δ |
| Smell during use | X | ○ | ○ | ○ | ○ | ○ |
| Moistening and spreading of the compounded solution | ○ | X | ○ | ○ | ○ | ○ |
| Wiping ability of the compounded solution | XA | ○ | ○ | XB | XB | ○ |
| Residual solution on the wiped surface | ○ | XA | ○ | XB | XB | ○ |
| Storage ability | ○ | ○ | ○ | ○ | ○ | ○ |

Major antimicrobial components in the plant essential oils in Table 1 are as follows:

Thyme oil: 37% by mass of carvacrol and 16% by mass of thymol.

Rosemary oil: 45% by mass of 1,8-cineol and 10% by mass of camphor.

Eucalyptus oil: 81% by mass of 1,8-cineol and 13% by mass of limonene.

The ε-polylysine used was a product of Chisso Corporation.

Examples 11 to 18

Compositions (Examples 11 to 18) were prepared by using the same composition as in Example 1 in Table 1 except that in place of thyme oil in Example 1, thymol, geraniol, hinokithiol, carvacrol, citral, eugenol, terpinene (terpinene)-4-ol or 1,8-cineol was incorporated as component (b) in an amount of 0.005% by mass, and any of the resultant compositions exhibited a good sterilizing effect and storage stability, and could be used preferably in respect of smell during use and feeling in use during wiping and washing.

What is claimed is:

1. A bactericide composition comprising (a) 0.0001 to 1 % by mass of polylysine, (b) 0.0001 to 1 % by mass of a plant essential oil, (c) 0.1 to 18 % by mass of an organic solvent and (d) 80 to 99 % by mass of water.

2. The bactericide composition according to claim 1, wherein the plant essential oil comprises at least one compound selected from the group consisting of thymol, geraniol, hinokithiol, carvacrol, citral, eugenol, terpinene (terpinene)-4-ol, 1,8-cineol, citronellal, citronellol, linalool, anethole, menthol, inenthone, carvone, camphor and limonene.

3. A bactericide composition comprising (a) 0.000 1 to 1 % by mass of polylysine, (b1) 0.0001 to 1% by mass of at least one compound selected from the group consisting of thymol, geraniol, hinokithiol, carvacrol, citral, eugenol, terpinene (terpinene)-4-ol, 1,8-cineol, citronellal, citronellol, linalool, anethole, menthol, menthone, carvone, camphor and limonene, (c) 0.1 to 18 % by mass of an organic solvent and (d) 80 to 99 % by mass of water.

4. The bactericide composition according to claim 1 further comprising a surfactant in an amount which is not higher than 0.1% by mass.

5. A packaged bactericide comprising the bactericide composition of claim 4 charged into a container equipped with a non-aerosol sprayer.

6. A method of sterilizing a hard surface comprising:

applying a composition comprising (a) 0.0001 to 1% by mass of polylysine, (b) 0.0001 to 1 % by mass of a plant essential oil, (c) 0.1 to 18 % by mass of an organic solvent and (d) 80 to 99 % by mass of water to the hard surface.

7. A method of sterilizing a hard surface, comprising applying the composition as claimed in claim 1 to the hard surface and wiping the composition from the hard surface.

8. The bactericide composition according to claim 3 further comprising a surfactant, wherein the content of a surfactant is not higher than 0.1 % by mass.

9. A packaged bactericide, comprising:

the bactericide composition of claim 8 charged into a container equipped with a non-aerosol sprayer.

10. A sterilizer, comprising:

the composition as claimed in claim 1 contained within a manually operated sprayer.

* * * * *